United States Patent
Wong

(10) Patent No.: US 11,350,860 B1
(45) Date of Patent: Jun. 7, 2022

(54) WRIST-WORN DEVICE AND METHOD FOR ACCURATE BLOOD OXYGEN SATURATION MEASUREMENT

(71) Applicant: Apple Inc., Cupertino, CA (US)

(72) Inventor: Earl Q. Wong, Vallejo, CA (US)

(73) Assignee: Apple Inc., Cupertino, CA (US)

( * ) Notice: Subject to any disclaimer, the term of this patent is extended or adjusted under 35 U.S.C. 154(b) by 267 days.

(21) Appl. No.: 16/687,012

(22) Filed: Nov. 18, 2019

Related U.S. Application Data

(63) Continuation of application No. 15/711,929, filed on Sep. 21, 2017, now abandoned.

(60) Provisional application No. 62/398,903, filed on Sep. 23, 2016.

(51) Int. Cl.
*A61B 5/1455* (2006.01)
*A61B 5/00* (2006.01)
*G01N 21/31* (2006.01)

(52) U.S. Cl.
CPC .......... *A61B 5/14551* (2013.01); *A61B 5/681* (2013.01); *A61B 5/6813* (2013.01); *G01N 21/31* (2013.01); *A61B 5/72* (2013.01); *G01N 2021/3181* (2013.01)

(58) Field of Classification Search
CPC .............. A61B 5/1455; A61B 5/14551; A61B 5/14552; A61B 5/0205; A61B 5/681; A61B 5/6813; A61B 5/6824; A61B 5/6825; A61B 5/6826; A61B 5/683; A61B 5/6831; A61B 5/72
See application file for complete search history.

(56) References Cited

U.S. PATENT DOCUMENTS

| | | | |
|---|---|---|---|
| 6,198,951 B1 | 3/2001 | Kosuda et al. | |
| 8,768,424 B2 | 7/2014 | Crowe et al. | |
| 8,920,332 B2* | 12/2014 | Hong | A61B 5/0205 600/500 |
| 9,314,197 B2 | 4/2016 | Fine et al. | |
| 2006/0069319 A1 | 3/2006 | Elhag et al. | |
| 2008/0208023 A1 | 8/2008 | Gruvac et al. | |
| 2009/0054751 A1 | 2/2009 | Babashan et al. | |
| 2009/0227852 A1 | 9/2009 | Glaser et al. | |
| 2010/0240972 A1 | 9/2010 | Neal | |
| 2014/0200423 A1* | 7/2014 | Eisen | A61B 5/14551 600/340 |
| 2014/0213863 A1 | 7/2014 | Loseu et al. | |

(Continued)

*Primary Examiner* — Chu Chuan Liu
(74) *Attorney, Agent, or Firm* — Kilpatrick Townsend & Stockton LLP

(57) ABSTRACT

Wrist-worn devices and methods for measuring blood oxygen saturation using a wrist-worn device compute blood oxygen saturation by processing an output signal from one or more photodetectors indicative of absorption of light by a finger interfaced with the one or more photodetectors. A method includes transmitting a first wavelength light into a finger from a first light emitter mounted to a wrist band of the wrist-worn device. A second wavelength light is transmitted into the finger from a second light emitter mounted to the wrist band. An output signal indicative of absorption by the finger of the first wavelength light and the second wavelength light is generated by one or more photodetectors interfaced with the finger and disposed on a housing of the wrist-worn device. The output signal is processed with a processor disposed in the housing to compute blood oxygen saturation.

20 Claims, 6 Drawing Sheets

(56) References Cited

U.S. PATENT DOCUMENTS

| | | |
|---|---|---|
| 2015/0141780 A1* | 5/2015 | Meyer ............... A61B 5/14552 600/323 |
| 2015/0265214 A1 | 9/2015 | Margreet et al. |
| 2016/0073954 A1 | 3/2016 | Meitav |
| 2018/0042513 A1 | 2/2018 | Connor |

* cited by examiner

WRIST-WORN DEVICE AND METHOD FOR ACCURATE BLOOD OXYGEN SATURATION MEASUREMENT

CROSS REFERENCE TO RELATED APPLICATION DATA

The present application is a Continuation of U.S. patent application Ser. No. 15/711,929 filed Sep. 21, 2017; which claims priority to U.S. Provisional Appln No. 62/398,903 filed Sep. 23, 2016; the full disclosures which are incorporated herein by reference in their entirety for all purposes.

BACKGROUND

Blood oxygen saturation is a vital medical parameter indicative of respiratory health. Blood oxygen saturation levels above 95% (at sea level) are considered normal for individuals without prior pulmonary pathology. Blood oxygen saturation levels below 90% indicate hypoxemia—a serious medical condition. Blood oxygen saturation levels in the mid 80's and below can be highly dangerous, frequently warranting immediate patient hospitalization.

Although current medically approved blood oxygen saturation meters are highly accurate, they typically have a cumbersome configuration, thereby inhibiting more ubiquitous monitoring of blood oxygen saturation. For example, blood oxygen saturation measurement devices often include a bulky finger clip into which a finger is inserted. Blood oxygen saturation meters are often powered by AAA or Li-ion batteries. An oxygen saturation meter typically employs first and second light emitting diodes (LEDs) and a photodetector. One side of the finger clip houses the LEDs and the other side of the finger clip houses the photodetector.

BRIEF SUMMARY

Wrist-worn devices and methods of measuring blood oxygen saturation using a wrist-worn device are described that compute blood oxygen saturation by processing an output signal from a photodetector indicative of absorption of light by a finger interfaced with the photodetector. The photodetector can be disposed on a housing or a wrist band of the wrist-worn device. The finger is interfaced with first and second light emitters mounted to a wrist band coupled to the housing. A first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) is transmitted into the finger by the first light emitter. A second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) is transmitted into the finger by the second light emitter. An output signal is generated by the photodetector indicative of absorption by the finger of the first wavelength light and the second wavelength light. The output signal is processed with a processor disposed in the housing to compute blood oxygen saturation. The wrist-worn device is operable to measure blood oxygen saturation without using a bulky finger clip, thereby enabling more regular monitoring of blood oxygen saturation.

Thus, in one aspect, a method of measuring blood oxygen saturation using a wrist-worn device is provided. The method includes providing a wrist-worn device that includes: (a) a housing having a front face and a rear face, (b) a band coupled to the housing and attachable to a wrist, (c) one or more photodetectors disposed on the housing, (d) a first light emitter that emits a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.), (e) a second light emitter that emits a second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.), and (f) a controller located within the housing. The first and second light emitters are located on the band. Each of the one or more photodetectors is responsive to the first wavelength light and/or the second wavelength light. The method includes placing a finger over the one or more photodetectors such that a first surface of the finger contacts the one or more photodetectors. The band is folded over the finger such that the first and second light emitters contact a second surface of the finger that is across from and opposite to the first surface of the finger. The first light emitter, second light emitter, and the one or more photodetectors are activated to measure absorption of the first wavelength light and the second wavelength light across the finger. Blood oxygen saturation is computed using the controller based on absorption of the first wavelength light and the second wavelength light by the finger.

The method of measuring blood oxygen saturation using a wrist-worn device can include detecting pulse rate. For example, the method can include processing an output signal from the one or more photodetectors to detect pulse rate. As another example, the wrist-worn device can include a separate heart rate sensor. Any suitable heart rate sensor can be included in the wrist-worn device. For example, a photoplethysmography (PPG) based heart rate sensor that includes one or more light emitters and one or more photodetectors can be included in the wrist-worn device. As another example, an electrocardiography (ECG) based heart rate sensor can be included in the wrist-worn device.

The method of measuring blood oxygen saturation using a wrist-worn device can include storing pulse rate data and/or blood oxygen saturation data for later display and/or processing. For example, the method can further include storing pulse rate data and/or blood oxygen saturation data within a memory device disposed in the housing.

The method of measuring blood oxygen saturation using a wrist-worn device can include transmitting the pulse rate data and/or the blood oxygen saturation data to an external data processing and/or storage device for storage, further processing, and/or display. For example, the method can include wirelessly transmitting the pulse rate data and/or the blood oxygen saturation data from the wrist-worn device to an external data processing and/or storage device for further processing and/or display.

In another aspect, a second method of measuring blood oxygen saturation using a wrist-worn device is provided. The second method includes transmitting a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) into a finger from a first light emitter mounted to a wrist band of the wrist-worn device. A second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) is transmitted into the finger from a second light emitter mounted to the wrist band. An output signal indicative of absorption by the finger of the first wavelength light and the second wavelength light is generated by a photodetector disposed on a housing of the wrist-worn device. The output signal is processed with a processor disposed in the housing to compute blood oxygen saturation.

The wrist-worn device can be configured so that the wrist-worn device remains attached to the wrist while the blood oxygen saturation is measured. For example, the first and second light emitters can be mounted to a segment of the wrist band that can be folded over the finger to interface the first and second light emitters with the finger while the finger is interfaced with the photodetector and the wrist band secures the housing to the wrist.

The second method of measuring blood oxygen saturation using a wrist-worn device can include detecting pulse rate. For example, the second method can include processing an output signal from the one or more photodetectors to detect pulse rate. As another example, the wrist-worn device can include a separate heart rate sensor. Any suitable heart rate sensor can be included in the wrist-worn device. For example, a photoplethysmography (PPG) based heart rate sensor that includes one or more light emitters and one or more photodetectors can be included in the wrist-worn device. As another example, an electrocardiography (ECG) based heart rate sensor can be included in the wrist-worn device.

The second method of measuring blood oxygen saturation using a wrist-worn device can include storing pulse rate data and/or blood oxygen saturation data for later display and/or processing. For example, the second method can further include storing pulse rate data and/or blood oxygen saturation data within a memory device disposed in the housing.

The second method of measuring blood oxygen saturation using a wrist-worn device can include transmitting the pulse rate data and/or the blood oxygen saturation data to an external data processing and/or storage device for further processing and/or display. For example, the method can include wirelessly transmitting the pulse rate data and/or the blood oxygen saturation data from the wrist-worn device to an external data processing and/or storage device for further processing and/or display.

In another aspect, a wrist-worn device configured for measuring blood oxygen saturation is provided. The wrist-worn device includes a housing, one or more photodetectors, a wrist band, a first light emitter, a second light emitter, and a controller. The housing has a wrist side and a display side opposite to the wrist side. The one or more photodetectors are disposed on the display side of the housing. Each of the one or more photodetectors is responsive to a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) and/or a second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.). The wrist band is coupled to the housing and attachable to a wrist to interface the wrist side of the housing with the wrist. The wrist band has a wrist side and an outer side opposite to the wrist side. The wrist side of the wrist band interfaces with the wrist when the wrist side of the housing is interfaced with the wrist. The first light emitter is operable to emit the first wavelength light. The first light emitter is disposed on the outer side of the wrist band so as to accommodate reconfiguring the wrist band to place the first light emitter into contact with a finger interfaced with the one or more photodetectors so that the one or more photodetectors are positioned to detect the first wavelength light transmitted through the finger by the first light emitter. The second light emitter is operable to emit the second wavelength light. The second light emitter is disposed on the outer side of the wrist band so as to accommodate reconfiguring the wrist band to place the second light emitter into contact with the finger interfaced with the one or more photodetectors so that the one or more photodetectors are positioned to detect the second wavelength light transmitted through the finger by the second light emitter. The controller is located within the housing. The controller is operatively coupled with the one or more photodetectors and the first and second light emitters. The controller is configured to control emission of light from the first and second light emitters and process one or more output signals from the one or more photodetectors to compute blood oxygen saturation based on absorption of the first wavelength light and the second wavelength light by the finger.

In many embodiments, the wrist-worn device includes a display unit disposed on the display side of the housing. For example, in many embodiments, the display unit is controlled by the controller and the controller is configured to cause the display unit to display the computed blood oxygen saturation.

In many embodiments, the wrist-worn device is configured to store blood oxygen saturation data that includes different blood oxygen saturation measurements. For example, the wrist-worn device can include a memory device disposed in the housing and operatively coupled with the controller. The controller can be configured to store blood oxygen saturation data within the memory device. The stored blood oxygen saturation data can include any suitable related data, for example, blood oxygen saturation, date/time of the blood oxygen saturation measurement, pulse rate, and/or date/time of the pulse rate measurement.

The wrist-worn device can be configured to transmit the stored blood oxygen saturation data to an external data processing and/or storage device for storage, further processing, and/or display. For example, the wrist-worn device can include a wireless communication unit operable to transmit the blood oxygen saturation data to an external data processing and/or storage device for storage, further processing, and/or display.

In many embodiments of the wrist-worn device, the controller is configured to process the output signal from the one or more photodetectors to detect pulse rate using a suitable known technique. As another example, the wrist-worn device can include a separate heart rate sensor. Any suitable heart rate sensor can be included in the wrist-worn device. For example, a photoplethysmography (PPG) based heart rate sensor that includes one or more light emitters and one or more photodetectors can be included in the wrist-worn device. As another example, an electrocardiography (ECG) based heart rate sensor can be included in the wrist-worn device.

The wrist-worn device can include a memory device disposed in the housing and operatively coupled with the controller. The controller can be configured to store blood oxygen saturation data and/or pulse rate data within the memory device. The wrist-worn device can include a wireless communication unit operable to transmit the blood oxygen saturation data and the pulse rate data to an external data processing and/or storage device for further processing and/or display.

The wrist-worn device can be configured to enable measurement of blood oxygen saturation without removing the wrist-worn device from the wrist. For example, the first and second light emitters can be mounted to a segment of the wrist band that can be folded over the finger to interface the first and second light emitters with the finger while the finger is interfaced with the one or more photodetectors and the wrist band secures the housing to the wrist.

In many embodiments, the wrist-worn device includes a rechargeable power source disposed within the housing. For example, the wrist-worn device can include an inductively charged power source disposed within the housing.

The details of one or more implementations are set forth in the accompanying drawings and the description below. Other features will be apparent from the description and drawings, and from the claims.

DETAILED DESCRIPTION

Figure 1:
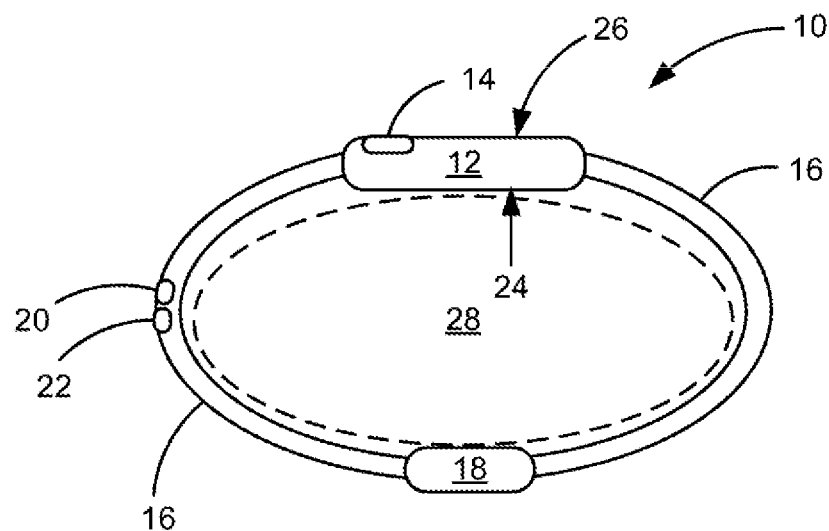
FIG. 1 illustrates a wrist-worn device configured to measure blood oxygen saturation, in accordance with many embodiments.

Wrist-worn devices configured to measure blood oxygen saturation and related methods are presented. The functionality of the wrist-worn devices described herein can be incorporated and/or combined into any suitable wrist-worn device (e.g., watch, smart watch, wrist-worn fitness tracking device). In many embodiments, a wrist-worn device includes one or more photodetectors located in any suitable location (e.g., on front face, on rear face, or wrist-band) on the wrist-worn device. Any suitable one or more photodetectors able to detect a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) and a second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) can be used. For example, an optical lens image sensor employed in existing smart devices can be employed to detect the light emitted by the first and second light emitters. The wrist-worn device can include an infrared cut filter that can be selectively employed when the optical lens image sensor is used to generate images and is bypassed when the wrist-worn device is used to measure blood oxygen saturation and the second light emitter emits an infrared wavelength light. As a result, infrared light that is transmitted through a finger can be detected by the wrist-worn device with high precision, thereby enabling high-precision measurement of blood oxygen saturation. In many embodiments, two light emitting diodes (LEDs) are built into the wrist-band of the wrist-worn device. A finger can be placed on the photodetector and the wrist-band folded to place the LEDs on the opposite side of the finger. The one or more photodetectors are used to generate an output signal having three independent portions. One portion of the output signal is generated by transmitting a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) from the first LED, through the finger, to the one or more photodetectors. Another portion of the output signal is generated by transmitting a second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) from the second LED, through the finger, to the one or more photodetectors. The final portion of the output signal is generated without either of the two LEDs emitting light. The three portions of the output signal are indicative of differences in absorption of the first wavelength light and the second wavelength light by the finger and are processed to determine the blood oxygen saturation using a known suitable technique. In many embodiments, the wrist-worn device includes a controller or processing unit that processes the output signal to calculate blood oxygen saturation using a suitable known technique. In many embodiments, the wrist-worn device includes a memory device for storing blood oxygen saturation measurements. The wrist-worn device can include a wireless transmitter that can be used to transmit blood oxygen saturation data to an external processing unit and/or storage device for further processing, storage, and/or display. The wrist-worn device can also be configured to process output from the one or more photodetectors to measure pulse rate using a suitable known technique. The wrist-worn device can also include a separate heart rate sensor (e.g., a photoplethysmography (PPG) based heart rate sensor, an electrocardiography (ECG) based heart rate sensor). The wrist-worn device can also include a rechargeable power source (e.g., an inductively charged power source).

Turning now to the drawing figures in which like reference numbers refer to like elements, FIG. 1 shows a side view of a wrist-worn device 10 configured to measure blood oxygen saturation, in accordance with many embodiments. The wrist-worn device 10 includes a main unit or housing 12, one or more photodetectors 14, a wrist band 16, a wrist band coupler 18, a first light emitting diode (LED) 20, and a second LED 22. The main unit 12 has a wrist side 24 and a display side 26 opposite to the wrist side 24. The one or more photodetectors 14 are disposed on the display side 26 of the main unit 12. The photodetector 14 is responsive to a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) emitted by the first LED 20 and to a second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) emitted by the second LED 22. The wrist band 16 is attached to the main unit 12 and can include the wrist band coupler 18, which can be used to reconfigure the wrist band 16 for mounting and demounting of the wrist-worn device 10 to a wrist 28.

Figure 2:
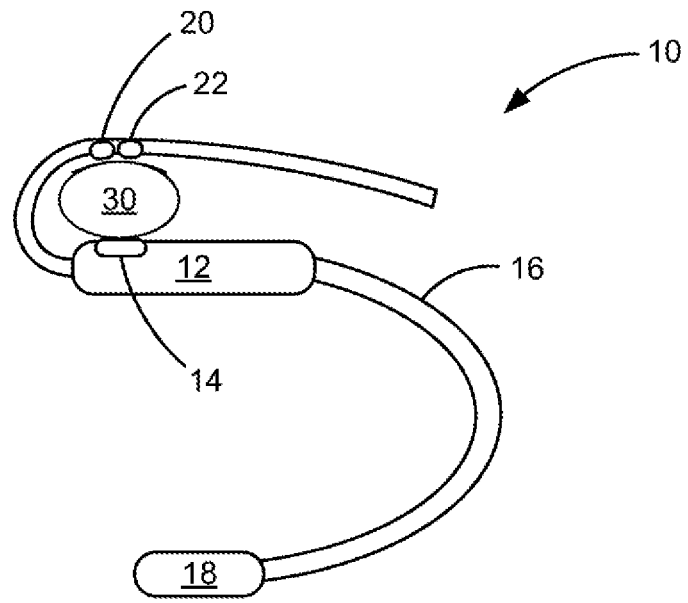
FIG. 2 illustrates the wrist-worn device of FIG. 1 with wrist-band mounted light emitting diodes and a photodetector of the wrist-worn device interfaced with a finger during a measurement of blood oxygen saturation.

FIG. 2 illustrates a finger 30 interfaced with the wrist-worn device 10 in a configuration to measure blood oxygen saturation via measurement of light absorption by the finger 30. In the illustrated configuration, one side of the finger 30 has been placed into contact with the one or more photodetectors 14 and the wrist band 16 folded to place the first LED 20 and the second LED 22 into contact with the finger 30 opposite to the one or more photodetectors 14. The first wavelength light is transmitted into the finger by the first LED 20. The second wavelength light is transmitted into the finger by the second LED 22. The one or more photodetectors 14 detect the resulting first wavelength light and the second wavelength light that emerges from the finger 30 and generates an output signal indicative of the first wavelength light and the second wavelength light detected. In many embodiments, the wrist-worn device 10 includes a controller or processing unit that processes the output signal from the one or more photodetectors 14 using a suitable known technique to determine blood oxygen saturation. In many embodiments, the wrist-worn device 10 includes a display unit disposed on the display side 26 of the main unit 12 and controllable by the controller or processing unit to display the measured blood oxygen saturation.

The one or more photodetectors 14 can have any suitable configuration and be employed in any suitable manner. For example, a single photodetector 14 responsive to both of the first wavelength light and the second wavelength light can be employed. The single photodetector 14 can be configured to simultaneously receive the first wavelength light and the second wavelength light and output one or more signals indicative of the amount of the first wavelength light and the amount of the second wavelength light received by the single photodetector 14. As another example, the emission of the first wavelength light from the first LED 20 and the emission of the second wavelength light from the second LED can be time-multiplexed such that only one of the first wavelength light and the second wavelength light are emitted at a time thereby allowing a single photodetector 14 to be employed that is not able to distinguish between the first wavelength light and the second wavelength light. As another example, the one or more photodetectors 14 can include an array of sensing elements, each of which can be responsive to a respective range of wavelengths of light.

Figure 3:
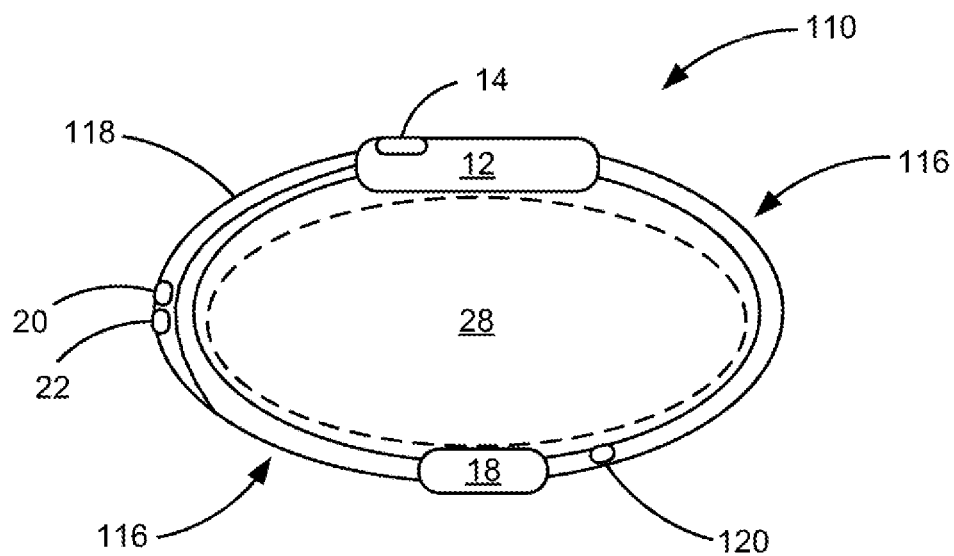
FIG. 3 illustrates another wrist-worn device configured to measure blood oxygen saturation, in accordance with many embodiments.

FIG. 3 shows a side view of a wrist-worn device 110 configured to measure blood oxygen saturation, in accordance with many embodiments. The wrist-worn device 110 is configured similar to the wrist-worn device 10, but includes a wrist band 116 that includes a separately foldable segment 118 to which the first LED 20 and the second LED 22 are mounted. The wrist-worn device can include a separate heart rate sensor 120 operatively coupled with the controller or processing unit to measure heart rate of the user. Any suitable heart rate sensor 120 can be employed, such as a photoplethysmography (PPG) based heart rate sensor or an electrocardiography (ECG) based heart rate sensor.

Figure 4:
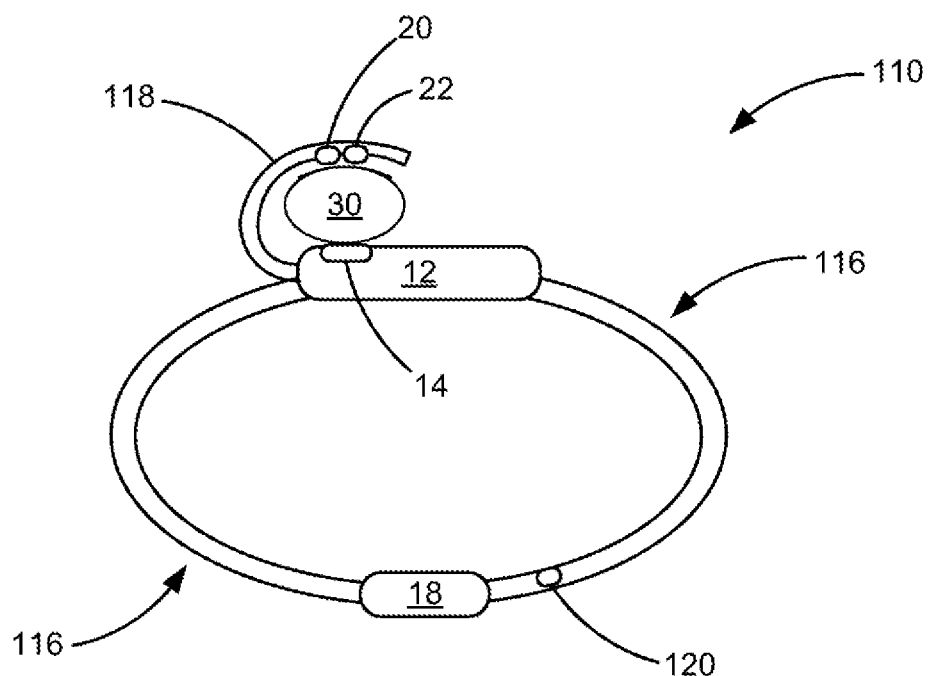
FIG. 4 illustrates the wrist-worn device of FIG. 3 with wrist-band segment mounted light emitting diodes and a photodetector of the wrist-worn device interfaced with a finger during a measurement of blood oxygen saturation.

FIG. 4 illustrates a finger 30 interfaced with the wrist-worn device 110 in a configuration to measure blood oxygen saturation via measurement of light absorption by the finger 30. In the illustrated configuration, one side of the finger 30 has been placed into contact with the one or more photodetectors 14 and the separately foldable segment 118 folded to place the first LED 20 and the second LED 22 into contact with the finger 30 opposite to the one or more photodetectors 14. The wrist-worn device 110 emits light from the first and second LEDs 20, 22 and processes a resulting signal generated by the one or more photodetectors 14 in the same way as described herein for the wrist-worn device 10.

Figure 5:
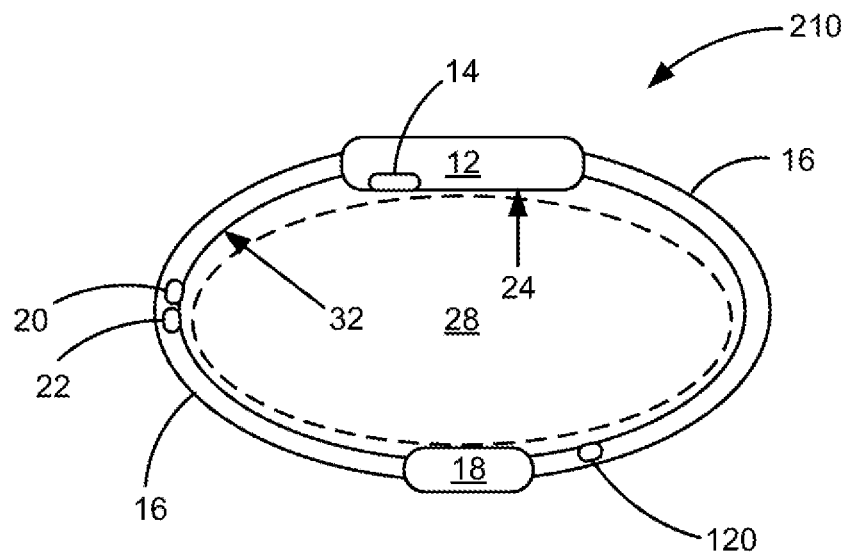
FIG. 5 illustrates another wrist-worn device configured to measure blood oxygen saturation, in accordance with many embodiments.

FIG. 5 shows a side view of a wrist-worn device 210 configured to measure blood oxygen saturation, in accordance with many embodiments. The wrist-worn device 210 is configured similar to the wrist-worn devices 10, 110, but with the one or more photodetectors 14 located on the wrist side 24 of the main unit 12 and the first and second LEDs 20, 22 being attached to a wrist side 32 of the wrist band 16. In an alternative embodiment of the wrist-worn device 210, the locations of the one or more photodetectors 14 and the first and second LEDs 20, 22 are switched relative to the locations shown in FIG. 5 so that the first and second LEDs 20, 22 are located on the wrist side 24 of the main unit 12 and the one or more photodetectors 14 are attached to the wrist side 32 of the wrist band 16.

Figure 6:
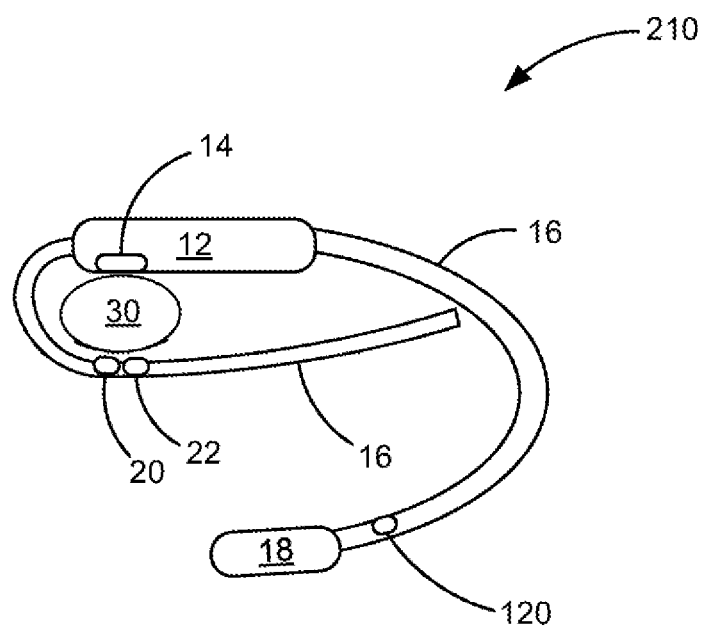
FIG. 6 illustrates the wrist-worn device of FIG. 5 with wrist-band mounted light emitting diodes and a photodetector of the wrist-worn device interfaced with a finger during a measurement of blood oxygen saturation.

FIG. 6 illustrates a finger 30 interfaced with the wrist-worn device 210 in a configuration to measure blood oxygen saturation via measurement of light absorption by the finger 30. In the illustrated configuration, one side of the finger 30 has been placed into contact with the one or more photodetectors 14 and the wrist band 16 folded to place the first LED 20 and the second LED 22 into contact with the finger 30 opposite to the one or more photodetectors 14. The wrist-worn device 210 emits light from the first and second LEDs 20, 22 and process a resulting signal generated by the one or more photodetectors 14 in the same way as described herein for the wrist-worn devices 10, 110.

Figure 7:
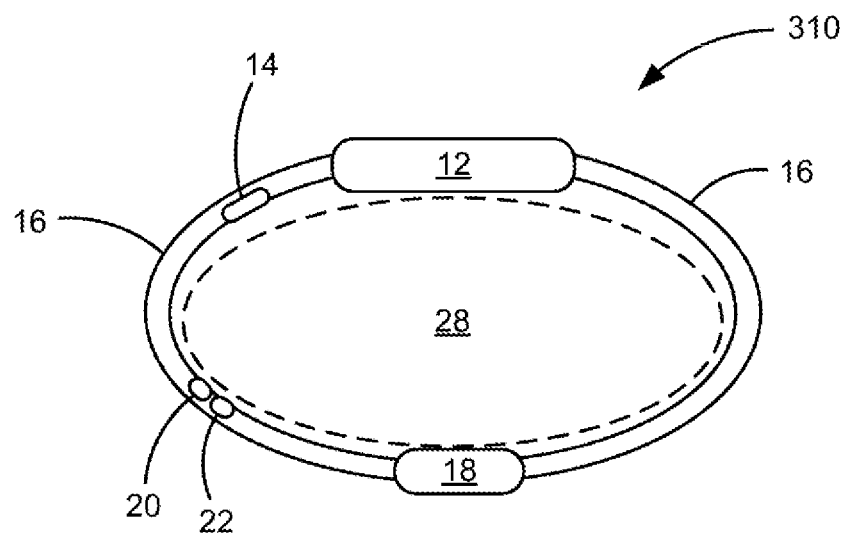
FIG. 7 illustrates another wrist-worn device configured to measure blood oxygen saturation, in accordance with many embodiments.

FIG. 7 shows a side view of a wrist-worn device 310 configured to measure blood oxygen saturation, in accordance with many embodiments. The wrist-worn device 310 is configured similar to the wrist-worn device 10, but with the photodetector 14 and the first and second LEDs 20, 22 mounted to the wrist band 16.

Figure 8:
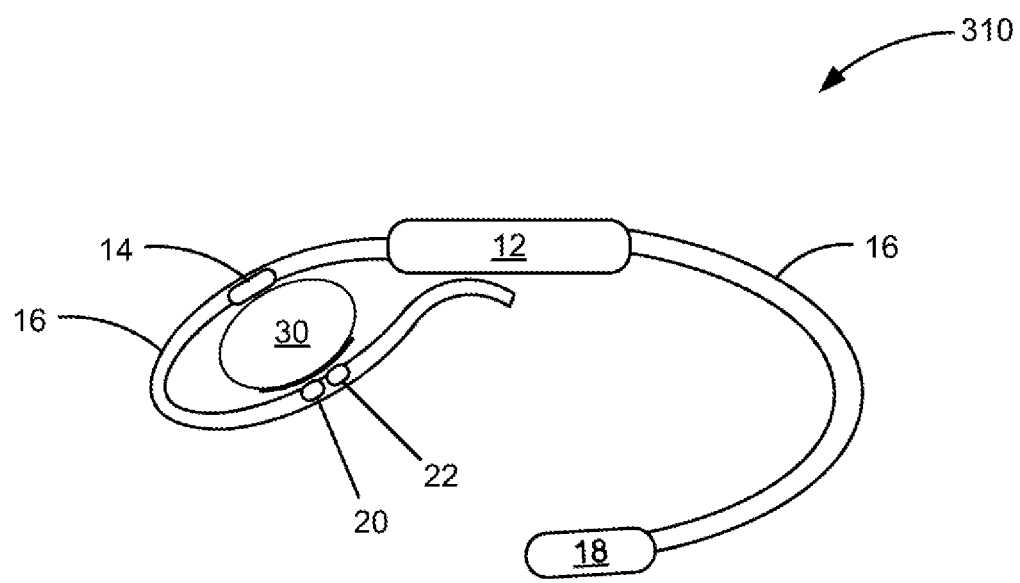
FIG. 8 illustrates the wrist-worn device of FIG. 7 with wrist-band mounted light emitting diodes and a wrist-band mounted photodetector of the wrist-worn device interfaced with a finger during a measurement of blood oxygen saturation.

FIG. 8 illustrates a finger 30 interfaced with the wrist-worn device 310 in a configuration to measure blood oxygen saturation via measurement of light absorption by the finger 30. In the illustrated configuration, one side of the finger 30 has been placed into contact with the one or more photodetectors 14 and the wrist band 16 folded to place the first LED 20 and the second LED 22 into contact with the finger 30 opposite to the one or more photodetectors 14. The wrist-worn device 310 emits light from the first and second LEDs 20, 22 and process the resulting signal(s) generated by the one or more photodetectors 14 in the same way as described herein for the wrist-worn device 10, 110, 210.

Figure 9:
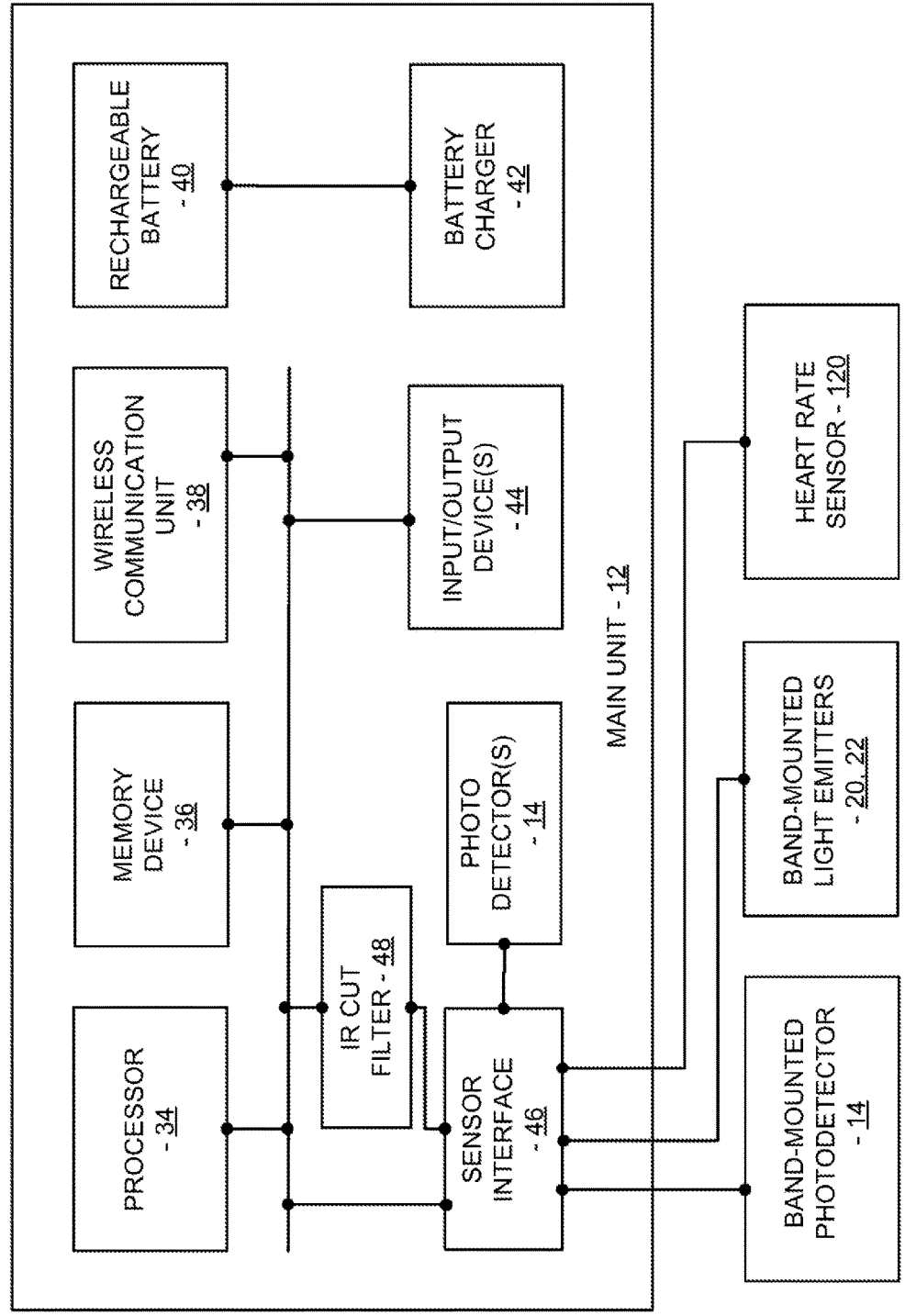
FIG. 9 is a simplified schematic diagram of components of a wrist-worn device for measuring blood oxygen saturation, in accordance with many embodiments.

FIG. 9 is a simplified schematic diagram of components that can be included in the wrist-worn device 10. Each of the other embodiments of the wrist-worn device 110, 210, 310 described herein can include any suitable combination of the components illustrated in FIG. 9. The components of the wrist-worn device 10 shown in FIG. 9 include the main unit 12, band mounted first and second LEDs 20, 22, optional heart rate sensor 120 (which can be mounted to the wrist band 16 or to the main unit 12), one or more photodetectors 14 (which can be mounted to the main unit 12 or the wrist band 16 as described herein). In the illustrated embodiment, the main unit 12 includes a processor 34, a memory device 36, a wireless communication unit 38, a rechargeable battery 40, a battery charger 42, one or more input/output devices 44, a sensor interface 46, and an infrared cut filter 48.

The memory device 36 can be used to store any suitable combination of instructions executable by the processor 34 and/or resulting measured blood oxygen saturation data and/or pulse data. For example, the memory device 36 can store instructions executable by the processor 34 for controlling operation of components of the wrist-worn device 10 (e.g., the first and second LEDs 20, 22, the wireless communication unit 38, the battery charger 42, the input/output device(s) 44, the one or more photodetectors 14, the heart rates sensor 120, and the infrared cut filter 48) and for processing the resulting output signal from the photodetector 14 to determine blood oxygen saturation and/or pulse rate using a suitable known technique. The memory device 36 can also store blood oxygen saturation data, which can include blood oxygen saturation measured at different times. In many embodiments, the stored blood oxygen saturation data includes date and time data indicating when the respective blood oxygen saturation data was measured. The memory device 36 can also store pulse data, which can include pulse rate measured at different times. In many embodiments, the pulse data includes data and time data indicating when the pulse rate was measured.

The wireless communication unit 38 can be used to wirelessly transmit blood oxygen saturation data and/or pulse data stored in the memory device 36 to an external device for storage, display, and/or further processing. For example, the wireless communication unit 38 can be used to transmit the blood oxygen saturation data and/or the pulse data to a smart phone for storage, display, further processing, or transmission over a communication network to a health care professional, who can evaluate the data in view of the medical history of the particular user.

Any suitable rechargeable battery 40 and battery charger 42 can be employed. For example, the rechargeable battery 40 can be a lithium ion battery and/or the battery charger 42 can be an inductive battery charger.

Any suitable input/output device(s) 44 can be employed. For example, the input/output device(s) 44 can include a touch screen device operable to display output (e.g., blood oxygen saturation, pulse rate, date/time of a blood oxygen saturation and/or pulse rate measurement) and to receive user input. The input/output devices 44 can also include a non-touch output display and suitable input devices such as push buttons.

Any suitable one or more photodetectors 14 can be used. For example, the photodetector 14 can be configured to capture images in addition to generating an output signal in response to the first wavelength light and the second wavelength light transmitted through the finger 30 by the first and second LEDs 20, 22. The sensor interface 46 can be any suitable device for interfacing the one or more photodetectors 14 with the processor 34. The infrared cut filter 48 can be selectively employed to filter the output signal from the one or more photodetectors 14 to filter out infrared light generated components when the photodetector 14 is used to generate image data. The infrared cut filter 48 can be bypassed when the one or more photodetectors 14 are used to generate a signal that is processed by the processor 34 to generate the blood oxygen saturation percentage and/or the pulse rate. Alternatively, the infrared cut filter 48 can be omitted entirely.

Figure 10:
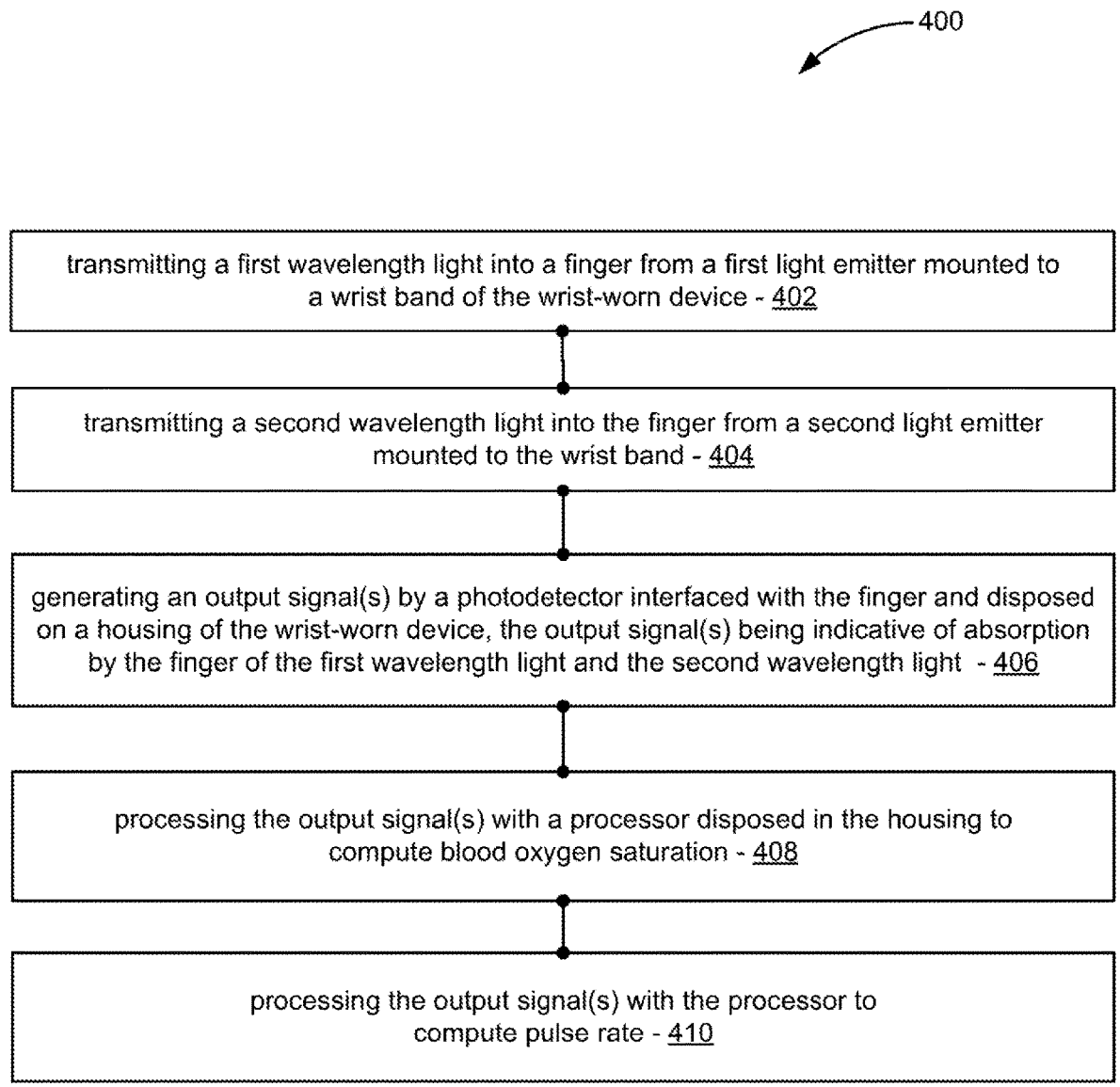
FIG. 10 is a simplified block diagram of a method of measuring blood oxygen saturation using a wrist-worn device, in accordance with many embodiments.

FIG. 10 is a simplified block diagram of a method 400 of measuring blood oxygen saturation using a wrist-worn device, in accordance with many embodiments. The acts of the method 400 can be accomplished using any suitable wrist-worn device, such as the wrist-worn devices 10, 110, 210, 310 described herein. The method 400 includes transmitting a first wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) into a finger 30 from a first light emitter 20 mounted to a wrist band 16 of the wrist-worn device (act 402). A second wavelength light (e.g., a suitable wavelength light such as a suitable infrared wavelength light such as 940 nm wavelength light, a suitable red wavelength light such as 660 nm wavelength light, a suitable green wavelength light, a suitable blue wavelength light, etc.) is transmitted into the finger 30 from a second light emitter 22 mounted to the wrist band (act 404). An output signal is generated by the photodetector 14 that is interfaced with the finger and disposed on a housing of the wrist-worn device. The output signal is indicative of absorption by the finger 30 of the first wavelength light and the second wavelength light (act 406). The output signal is processed with a processor 34 disposed in the housing to compute blood oxygen saturation using a suitable known technique (act 408). In some embodiments, the output signal is further processed with the processor 34 to compute pulse rate using a suitable known technique (act 410).

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

While the exemplary embodiments have been described in some detail, by way of example and for clarity of understanding, those of skill in the art will recognize that a variety of modifications, adaptations, and changes may be employed.

What is claimed is:

1. A method of measuring blood oxygen saturation using a wrist-worn device, the method comprising:
   providing a wrist-worn device comprising a housing having a wrist face and a display face opposite to the wrist face, a wrist band coupled to the housing and configured to be attached to a wrist to interface the wrist face of the housing with the wrist, the wrist band having a wrist side and an outer side opposite to the wrist side, the wrist side of the wrist band interfacing with the wrist when the wrist face of the housing is interfaced with the wrist, one or more photodetectors, a first light emitter that emits a first wavelength light, a second light emitter that emits a second wavelength light, and a controller located within the housing; wherein the first and second light emitters and/or the one or more photodetectors are located on the wrist band and wherein the one or more photodetectors are responsive to the first wavelength light and the second wavelength light;

placing a finger over the photodetector such that a first surface of the finger contacts the photodetector;

folding the wrist band over the finger such that the first and second light emitters contact a second surface of the finger that is across from and opposite to the first surface of the finger;

activating the first light emitter, the second light emitter, and the one or more photodetectors to measure absorption of first wavelength light and the second wavelength light by the finger; and computing blood oxygen saturation, by using the controller, based on the measured absorption of the first wavelength light and the second wavelength light by the finger.

2. The method of claim 1, further comprising processing an output signal from the one or more photodetectors to detect pulse rate.

3. The method of claim 2, further comprising storing pulse rate data and blood oxygen saturation data within a memory device disposed in the housing.

4. The method of claim 3, further comprising wirelessly transmitting the pulse rate data and/or the blood oxygen saturation data from the wrist-worn device to an external data processing and/or storage device.

5. A method of measuring blood oxygen saturation using a wrist-worn device, the method comprising:

transmitting a first wavelength light into a finger from a first light emitter mounted to a wrist band or a housing of the wrist-worn device, wherein the housing has a wrist face and a display face opposite to the wrist face, wherein the wrist band is coupled to the housing and configured to be attached to a wrist to interface the wrist face of the housing with the wrist, wherein the wrist band has a wrist side and an outer side opposite to the wrist side, and wherein the wrist side of the wrist band interfaces with the wrist when the wrist face of the housing is interfaced with the wrist;

transmitting a second wavelength light into the finger from a second light emitter;

generating, by one or more photodetectors interfaced with the finger, an output signal indicative of absorption by the finger of the first wavelength light and the second wavelength light; and processing the output signal with a processor disposed in the housing to compute blood oxygen saturation, wherein the first and second light emitters and/or the one or more photodetectors are mounted to the wrist band.

6. The method of claim 5, wherein the first and second light emitters are mounted to a segment of the wrist band configured to be folded over the finger to interface the first and second light emitters with the finger while the finger is interfaced with the one or more photodetectors and the wrist band secures the housing to a wrist.

7. The method of claim 5, further comprising processing the output signal with the processor to detect pulse rate.

8. The method of claim 7, further comprising storing pulse rate data and blood oxygen saturation data within a memory device disposed in the housing.

9. The method of claim 8, further comprising wirelessly transmitting the pulse rate data and the blood oxygen saturation data from the wrist-worn device to an external data processing and/or storage device.

10. The method of claim 5, further comprising storing blood oxygen saturation data within a memory device disposed in the housing.

11. The method of claim 10, further comprising wirelessly transmitting the blood oxygen saturation data from the wrist-worn device to an external data processing and/or storage device.

12. A wrist-worn device configured for measuring blood oxygen saturation, the wrist-worn device comprising:

a housing having a wrist side and a display side opposite to the wrist side;

one or more photodetectors responsive to a first wavelength light and a second wavelength light;

a wrist band coupled to the housing and configured to be attached to a wrist to interface the wrist side of the housing with the wrist, the wrist band having a wrist side and an outer side opposite to the wrist side, the wrist side of the wrist band interfacing with the wrist when the wrist side of the housing is interfaced with the wrist;

a first light emitter operable to emit the first wavelength light and disposed to accommodate reconfiguring the wrist band to place the first light emitter into contact with a finger interfaced with the one or more photodetectors so that the one or more photodetectors are positioned to detect the first wavelength light transmitted through the finger by the first light emitter;

a second light emitter operable to emit the second wavelength light and disposed to accommodate reconfiguring the wrist band to place the second light emitter into contact with the finger interfaced with the one or more photodetectors so that the one or more photodetectors are positioned to detect the second wavelength light transmitted through the finger by the second light emitter; and a controller located within the housing and operatively coupled with the one or more photodetectors and the first and second light emitters, the controller is configured to control emission of light from the first and second light emitters and process an output signal from the one or more photodetectors to compute blood oxygen saturation based on absorption of the first wavelength light and the second wavelength light by the finger, wherein the first and second light emitters and/or the one or more photodetectors are mounted to the wrist band.

13. The wrist-worn device of claim 12, comprising a display unit disposed on the display side of the housing, the display unit being controlled by the controller, the controller being to cause the display unit to display the computed blood oxygen saturation.

14. The wrist-worn device of claim 12, comprising a memory device disposed in the housing and operatively coupled with the controller, the controller being configured to store blood oxygen saturation data within the memory device.

15. The wrist-worn device of claim 14, comprising a wireless communication unit operable to transmit the blood oxygen saturation data to an external data processing and/or storage device.

16. The wrist-worn device of claim 12, wherein the controller is configured to process the output signal from the one or more photodetectors to detect pulse rate.

17. The wrist-worn device of claim 16, comprising a memory device disposed in the housing and operatively coupled with the controller, the controller being configured to store blood oxygen saturation data and pulse rate data within the memory device.

18. The wrist-worn device of claim 17, comprising a wireless communication unit operable to transmit the blood oxygen saturation data and the pulse rate data to an external data processing and/or storage device.

19. The wrist-worn device of claim 12, wherein the first and second light emitters are mounted to a segment of the wrist band configured to be folded over the finger to interface the first and second light emitters with the finger while the finger is interfaced with the one or more photodetectors and the wrist band secures the housing to the wrist.

20. The wrist-worn device of claim 12, comprising an inductively charged power source disposed within the housing.

* * * * *